(12) United States Patent
Hassan et al.

(10) Patent No.: US 8,461,408 B2
(45) Date of Patent: *Jun. 11, 2013

(54) SYSTEM AND PROCESS FOR ALKYLATION

(75) Inventors: Abbas Hassan, Sugar Land, TX (US);
Ebrahim Bagherzadeh, Sugar Land, TX (US); Rayford G. Anthony, College Station, TX (US); Gregory Borsinger, Chatham, NJ (US); Aziz Hassan, Sugar Land, TX (US)

(73) Assignee: H R D Coporation, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/586,283

(22) Filed: Aug. 15, 2012

(65) Prior Publication Data
US 2012/0310028 A1 Dec. 6, 2012

Related U.S. Application Data

(63) Continuation of application No. 12/138,240, filed on Jun. 12, 2008, now Pat. No. 8,269,057.

(60) Provisional application No. 60/946,457, filed on Jun. 27, 2007.

(51) Int. Cl.
*C07C 2/60* (2006.01)
*C07C 2/62* (2006.01)

(52) U.S. Cl.
USPC ........... 585/720; 585/723; 585/726; 585/727; 585/730; 585/731

(58) Field of Classification Search
USPC .................. 585/720, 723, 726, 727, 730, 731
See application file for complete search history.

(56) References Cited

U.S. PATENT DOCUMENTS

| 3,781,320 | A | | 12/1973 | Irwin |
| 3,887,167 | A | | 6/1975 | Irwin |
| 4,017,263 | A | * | 4/1977 | Holmes et al. ................ 422/202 |

(Continued)

FOREIGN PATENT DOCUMENTS

| CA | 1076506 | 4/1980 |
| CA | 2677613 | 5/2012 |

(Continued)

OTHER PUBLICATIONS

The English abstract of FR002835762A1, Aug. 18, 2003, Guillaume et al.*

(Continued)

*Primary Examiner* — Thuan D Dang
(74) *Attorney, Agent, or Firm* — Porter Hedges LLP; Timothy S. Westby

(57) ABSTRACT

A method for alkylating a hydrocarbon comprising at least one isoparaffin and at least one olefin that includes introducing a liquid catalyst and the hydrocarbon into a high shear device; processing the liquid catalyst and the hydrocarbon in the high shear device to form an emulsion comprising droplets of hydrocarbon dispersed in the liquid catalyst; introducing the emulsion into a vessel operating under suitable alkylation conditions whereby at least a portion of the isoparaffin is alkylated with the olefin to form alkylate, wherein suitable alkylation conditions comprise a bulk reaction temperature of from about 38° C. to about 90° C. and a bulk reaction pressure in the range of from about 1379 kPa to about 34 MPa; and removing a product stream comprising alkylate from the vessel.

17 Claims, 2 Drawing Sheets

U.S. PATENT DOCUMENTS

| | | | |
|---|---|---|---|
| 4,950,831 | A | 8/1990 | Staton et al. |
| 5,075,027 | A | 12/1991 | Dixit |
| 5,345,027 | A | 9/1994 | Child et al. |
| 5,534,657 | A * | 7/1996 | Randolph et al. ............ 585/723 |
| 5,538,191 | A | 7/1996 | Holl |
| 5,877,350 | A | 3/1999 | Langer et al. |
| 6,368,366 | B1 | 4/2002 | Langer et al. |
| 6,368,367 | B1 | 4/2002 | Langer et al. |
| 6,383,237 | B1 | 5/2002 | Langer et al. |
| 6,530,964 | B2 | 3/2003 | Langer et al. |
| 6,742,774 | B2 | 6/2004 | Holl |
| 8,269,057 | B2 | 9/2012 | Hassan et al. |
| 2003/0043690 | A1 | 3/2003 | Holl et al. |
| 2004/0052158 | A1 | 3/2004 | Holl |
| 2005/0033069 | A1 | 2/2005 | Holl et al. |
| 2005/0283025 | A1 | 12/2005 | Hirota et al. |
| 2006/0245991 | A1 | 11/2006 | Holl |
| 2007/0030322 | A1 | 2/2007 | Lee et al. |

FOREIGN PATENT DOCUMENTS

| | | |
|---|---|---|
| EA | 017474 | 12/2012 |
| EP | 1604969 | 12/2005 |
| FR | 2835762 | 8/2003 |
| JP | 10195205 | 7/1998 |
| JP | 11106407 | 4/1999 |
| WO | 02064708 A2 | 8/2002 |

OTHER PUBLICATIONS

IKA-Rotor-Stator Generators—2003 Processing Catalog; 38 pages.
"Cavitation: A technology on the horizon," Current Science 91 (No. 1) 35-46 (2006).
GCC Examination Report dated Aug. 13, 2011 for corresponding GCC Application No. GCC/P/2008/11170; 6 pages.
Canadian Office Action dated Jan. 26, 2011 for corresponding Canadian Application No. 2677613; 2 pages.
International Search Report, International Application No. PCT/US2008/067992, dated Jan. 21, 2009; 4 pages.
Office Action dated Jun. 25, 2009 for U.S. Appl. No. 12/142,447.
Office Action dated Jan. 7, 2010 for U.S. Appl. No. 12/142,447.
Office Action dated May 13, 2010 for U.S. Appl. No. 12/142,447.
Office Action dated Feb. 4, 2010 for U.S. Appl. No. 12/492,721.
Office Action dated Feb. 18, 2010 for U.S. Appl. No. 12/635,433.
Office Action dated Feb. 18, 2010 for U.S. Appl. No. 12/635,454.
Office Action dated May 14, 2010 for U.S. Appl. No. 12/137,441.
Office Action dated Feb. 19, 2010 for U.S. Appl. No. 12/144,459.
Office Action dated Sep. 2, 2009 for U.S. Appl. No. 12/142,433.
Office Action dated Jan. 29, 2010 for U.S. Appl. No. 12/142,433.
Office Action dated May 24, 2010 for U.S. Appl. No. 12/142,433.
Office Action dated Apr. 30, 2010 for U.S. Appl. No. 12/141,191.
Office Action dated Oct. 27, 2009 for U.S. Appl. No. 12/142,120.
Office Action dated May 5, 2010 for U.S. Appl. No. 12/571,537.
Office Action dated Feb. 24, 2011 for U.S. Appl. No. 12/796,358 (13 pgs.).
Office Action dated Feb. 29, 2012 for U.S. Appl. No. 12/146,733 (8 pgs.).
Office Action dated Jun. 3, 2011 for U.S. Appl. No. 12/568,155 (11 pgs.).
Office Action dated Jun. 2, 2011 for U.S. Appl. No. 12/427,286 (12 pgs.).
Office Action dated Jun. 3, 2011 for U.S. Appl. No. 12/568,280 (16 pgs.).
Office Action dated Sep. 19, 2011 for U.S. Appl. No. 12/138,240 (7 pgs.).
Office Action dated Apr. 21, 2011 for U.S. Appl. No. 12/138,240 (6 pgs.).
Notice of Allowance dated Jun. 29, 2012 for corresponding U.S. Appl. No. 12/138,240 (8 pgs.).
Chinese Office Action dated Jun. 29, 2012 for corresponding Chinese Application No. 200880011181.0 (9 pgs.).
Chinese Office Action dated Jan. 17, 2013 for corresponding Chinese Application No. 200880011181.0 (11 pgs.).
Notice of Allowance dated Jul. 31, 2012 for corresponding Eurasian Application No. 200901437 (3 pgs.).
Eurasian Office Action dated Mar. 30, 2012 for corresponding Eurasian Application No. 200901437 (2 pgs.).
Japanese Office Action dated Jul. 10, 2012 for corresponding Japanese Application No. 2010511432 (5 pgs.).
Kaisha, Maruzen "Experimental Chemistry 7," Japan, dated May 20, 1956, pp. 228-229 (4 pgs.).
European Search Report dated Mar. 1, 2013 for corresponding European Application No. EP08771799.7 (9 pgs.).
Sprow, F.B., "Role of Interfacial Area in Sulfuric Acid Alkylation," Industrial & Engineering Chemistry Product Research and Development, vol. 8, No. 2, dated Apr. 1, 1969, pp. 254-257 (4 pgs.).
IKA, "High Shear Mixers, Homogenizers and Dispersers, Dispax Reactor," Retrieved from <http://web.archive.org/web/20030428222302/http://ikausa.com/dr.htm> on Apr. 28, 2003 (2 pgs.).
Mosby, et al., "Alkylation of Isobutane with 1-Butene Using Sulfuric Acid as Catalyst at High Rates of Agitation," Industrial & Engineering Chemistry Product Research and Development, vol. 5, No. 2, dated Jun. 1, 1966, pp. 183-190 (8 pgs.).
Shlegeris, et al., "Alkylation of Isobutane with Various Olefins in the Presence of Sulfuric Acid," Industrial & Engineering Chemistry Product Research and Development, vol. 8, No. 1, dated Jan. 1, 1969, pp. 92-98 (7 pgs.).
IKA-DRS Reactors website http://www.ikausa.com/dr.him, on Sep. 8, 2010 (2 pgs.).
IKA, "Introduction to IKA's Three Stage Dispax Reactor," Retrieved from <http://www.ikausa.com/pdfs/process/dr%202000-Homogenizing-Dispersing-Suspending-Emulsifying.pdf> on Aug. 22, 2012 (12 pgs.).

* cited by examiner

SYSTEM AND PROCESS FOR ALKYLATION

CROSS-REFERENCE TO RELATED APPLICATIONS

This application is a continuation application of U.S. patent application Ser. No. 12/138,240, filed Jun. 12, 2008, which application claims the benefit under 35 U.S.C. §119(e) of U.S. Provisional Patent Application No. 60/946,457 entitled "High Shear Alkylation Process," filed Jun. 27, 2007. The disclosure of each application is hereby incorporated herein by reference in entirety for all purposes.

STATEMENT REGARDING FEDERALLY SPONSORED RESEARCH OR DEVELOPMENT

Not Applicable.

BACKGROUND OF THE INVENTION

1. Technical Field

The present invention generally relates to alkylation. More particularly, the present invention relates to a high shear system and process for accelerating alkylation of a feedstock comprising isoparaffins and olefins thereby increasing the octane number of the feedstock.

2. Background of the Invention

It is well known in the petroleum refining arts to catalytically crack heavy petroleum fractions, such as vacuum gas oil, or even in some cases atmospheric resid, in order to convert a substantial proportion thereof to a wide range of petroleum fractions. The light products from hydrocracking are rich in isobutane. Isobutane is a primary feedstock for motor fuel alkylation processes, which produces an excellent and environmentally superior gasoline-blending component.

Early alkylation units were built in conjunction with fluid catalytic cracking units to take advantage of the light end by-products of the cracking units: isoparaffins and olefins. Where the petroleum fraction being catalytically cracked contains sulfur, the products of catalytic cracking will also likely contain sulfur impurities. Hydrotreating is used for removal of undesirable components, including sulfur and nitrogen.

In general, hydrofinishing of FCC gasoline lowers the octane number thereof. Smaller molecules such as isobutane and propylene or butylenes can be recombined to meet specific octane requirements of fuels by processes such as alkylation or less commonly, dimerization. Octane grade of gasoline can also be improved by catalytic reforming, which strips hydrogen out of hydrocarbons to produce aromatics, which have much higher octane ratings.

Alkylation is the process of reacting light olefins with iso-butane to produce an alkylate product high in iso-octane. In alkylation, an alkyl group is added to an organic molecule (typically an aromatic or olefin). Thus an isoparaffin can be reacted with an olefin to provide an isoparaffin of higher molecular weight. Industrially, the concept depends on the reaction of a C2 to C5 olefin with isobutane in the presence of an acidic catalyst to produce an alkylate. This alkylate is a valuable blending component in the manufacture of gasolines due to its high octane rating and sensitivity to octane-enhancing additives. This motor fuel alkylate, which is ideal for producing reformulated gasoline, is suitable for gasoline blending because of its high octane and low vapor pressure.

Alkylate gasolines, such as those produced by the processes discussed above, are rich in isoparaffins and contain essentially no sulfur and aromatics. Generally exhibiting strong sensitivity to octane-enhancing additives, alkylate gasolines are prime candidates for blending into motor gasolines to meet increasingly stringent environmental regulations restricting gasoline vapor pressure and aromatics content. However, these alkylate gasolines are not suitable for use as blending stocks until they are free from the acid components of the alkylation catalyst. Specifically, the Lewis acid component of the alkylation catalyst complexes employed in common processes must be removed before the alkylate product can be blended into gasoline.

Standard alkylation processes have a continuous acid phase. However, U.S. Pat. No. 5,345,027 describes an alkylation process comprising a viscous acid catalyst dispersed in a continuous hydrocarbon phase.

Accordingly, there is a need in the industry for improved processes and systems for the commercially important alkylation of isoparaffins.

SUMMARY

High shear systems and methods for enhancing isoparaffin alkylation are disclosed. In accordance with certain embodiments a method for alkylating a hydrocarbon comprising at least one isoparaffin and at least one olefin, the method comprising introducing liquid acid catalyst and the hydrocarbon into a high shear reactor; forming an emulsion comprising droplets comprising hydrocarbon in a continuous acid phase, wherein the droplets have a mean diameter of less than about 5 μm; introducing the emulsion into a vessel operating under suitable alkylation conditions whereby at least a portion of the isoparaffin is alkylated with the olefin to form alkylate; and removing a product stream comprising alkylate from the vessel. The isoparaffin may contain from 4 to 8 carbon atoms. The olefin may contain from 2 to 12 carbon atoms. In embodiments, the at least one isoparaffin comprises isobutane and the at least one olefin comprises butene. Suitable alkylation conditions may comprise a temperature of from about 0° C. to about 90° C. and a pressure in the range of from about 345 kPa to about 3447 kPa. The catalyst may comprise an acid selected from sulfuric acid, hydrofluoric acid, $BF_3$, $SbF_5$, and $AlCl_3$. The droplets in the emulsion may have a mean diameter of less than 400 nm, or no more than 100 nm. Forming the emulsion may comprise subjecting the hydrocarbon and acid to high shear mixing at a tip speed of at least 22.9 m/s, or at least 40 m/s. The high shear mixing may produce a local pressure of at least about 1034 MPa at the tip. Forming the emulsion may comprise subjecting a mixture comprising the hydrocarbon and the acid to a shear rate of greater than about 20,000 $s^{-1}$. In embodiments, forming the emulsion comprises an energy expenditure of at least 1000 $W/m^3$. The alkylation may occur at a velocity at least 5 fold greater than that of a similar method wherein the hydrocarbon and liquid acid catalyst are not subjected to high shear mixing.

Also disclosed is a system for the alkylation of a hydrocarbon comprising at least one isoparaffin and at least one olefin, the system comprising at least one external high shear mixing device comprising at least one rotor and at least one stator separated by a shear gap, wherein the shear gap is the minimum distance between the at least one rotor and the at least stator, and wherein the high shear mixing device is capable of producing a tip speed at the tip of the at least one rotor of greater than 22.9 m/s (4,500 ft/min), a pump configured for delivering a pressurized liquid stream comprising liquid acid catalyst to the at least one high shear mixing device; and a vessel configured for receiving an emulsion from the high shear mixing device. The shear gap may be in the range of from about 0.02 mm to about 5 mm. The high shear mixing device may be configured to produce an emulsion comprising droplets having a mean diameter of less than 1 micron, wherein the emulsion comprises hydrocarbon droplets dispersed in a continuous liquid phase comprising acid catalyst or wherein the emulsion comprises droplets comprising acid catalyst in a continuous liquid phase comprising hydrocarbon. The at least one high shear mixing device may be configured for operating at a flow rate of at least 300 L/h. The at least one high shear mixing device may be configured to provide an energy expenditure greater than 1000 W/m$^3$. In embodiments, the at least one high shear mixing device comprises at least two rotors and at least two stators.

The process employs an external high shear mechanical reactor to provide enhanced time, temperature and pressure conditions resulting in accelerated chemical reactions between multiphase reactants.

In some embodiments, the system further comprises a pump configured for delivering a liquid stream comprising acid catalyst to the high shear mixing device. In some embodiments, the system further comprises a vessel configured for receiving the emulsion from the high shear device. Some embodiments of the system potentially make possible the alkylation of feedstock without the need for large volume reactors, via use of an external pressurized high shear reactor.

Embodiments of the disclosure pertain to a method for alkylating a hydrocarbon comprising at least one isoparaffin and at least one olefin that may include introducing a liquid catalyst and the hydrocarbon into a high shear device; processing the liquid catalyst and the hydrocarbon in the high shear device to form an emulsion comprising droplets of hydrocarbon dispersed in the liquid catalyst; introducing the emulsion into a vessel operating under suitable alkylation conditions whereby at least a portion of the isoparaffin is alkylated with the olefin to form alkylate, wherein suitable alkylation conditions comprise a bulk reaction temperature of from about 38° C. to about 90° C. and a bulk reaction pressure in the range of from about 1379 kPa to about 34 MPa; and removing a product stream comprising alkylate from the vessel.

The at least one isoparaffin may contain from 4 to 8 carbon atoms. The at least one olefin may contain from 2 to 12 carbon atoms. In aspects, the at least one isoparaffin may be isobutane and the at least one olefin may be butene. The liquid catalyst may include an acid selected from hydrofluoric acid, $BF_3$, $SbF_5$, and $AlCl_3$. In aspects, the droplets may have a mean diameter of no more than 100 nm.

In forming the emulsion, the method may also include subjecting the hydrocarbon and acid to high shear mixing at a tip speed of at least 22.9 m/s and to a shear rate of greater than about 20,000 s$^{-1}$. The high shear device may produce a local pressure of at least about 1034 MPa at the tip. The high shear device may include a rotor and a stator separated by a shear gap. The droplets may have a mean diameter in the range of about 0.1 µm to about 5 µm. The shear gap may have a width in the range of from about 0.02 mm to about 5 mm. The rotor and/or the stator may be configured with at least one toothed surface.

Other aspects of the disclosure pertain to a method for alkylating a hydrocarbon comprising at least one isoparaffin and at least one olefin that may include introducing a liquid catalyst selected from the group consisting of hydrofluoric acid, $BF_3$, $SbF_5$, $AlCl_3$, and combinations thereof, and the hydrocarbon into a high shear device; processing the liquid catalyst and the hydrocarbon in the high shear device to form an emulsion comprising droplets having a mean diameter less than about 5 µm; and transferring the emulsion from the high shear device into a vessel operating under suitable alkylation conditions whereby at least a portion of the isoparaffin is alkylated with the olefin to form alkylate.

The at least one isoparaffin may have from 4 to 8 carbon atoms. The at least one olefin may have from 2 to 12 carbon atoms. The method may further include removing a product stream comprising alkylate from the vessel. In aspects, the droplets may have a mean diameter of no more than 100 nm.

The high shear device may include a rotor and a stator separated by a shear gap in the range of from about 0.02 mm to about 5 mm. The rotor and/or the stator may include at least one toothed surface. In aspects, the emulsion may include hydrocarbon droplets dispersed in the liquid catalyst, wherein the mean diameter is less than 1 micron. In other aspects, the emulsion may include catalyst droplets dispersed in the hydrocarbon, wherein the mean diameter is less than 1 micron. In yet other aspects, the mean diameter may also be greater than about 0.1 µm.

In still other embodiments, the present disclosure pertains to a method for alkylating a hydrocarbon comprising at least one isoparaffin and at least one olefin that may include introducing a liquid catalyst and the hydrocarbon into a high shear device, wherein the liquid catalyst comprises an acid selected from the group consisting of sulfuric acid, hydrofluoric acid, $BF_3$, $SbF_5$, $AlCl_3$, and combinations thereof; forming an emulsion comprising hydrocarbon droplets dispersed in the liquid catalyst, wherein the droplets have a mean diameter of less than about 5 µm; and introducing the emulsion into a vessel operating under suitable alkylation conditions whereby at least a portion of the isoparaffin is alkylated with the olefin to form alkylate, wherein suitable alkylation conditions comprise a bulk reaction temperature of from about 38° C. to about 90° C. and a bulk reaction pressure in the range of from about 1379 kPa to about 34 MPa. In aspects, the mean diameter may also be greater than about 0.1 µm.

Certain embodiments of an above-described method or system potentially provide for more optimal time, temperature and pressure conditions than are otherwise possible, and which potentially increase the rate of the liquid/liquid or liquid/liquid/solid phase process. Certain embodiments of the above-described methods or systems potentially provide overall cost reduction by operating at lower temperature and/or pressure, providing increased product per unit of catalyst consumed, decreased reaction time, decreased olefin excess used, and/or reduced capital and/or operating costs. These and other embodiments and potential advantages will be apparent in the following detailed description and drawings.

BRIEF DESCRIPTION OF THE DRAWINGS

For a more detailed description of the preferred embodiment of the present invention, reference will now be made to the accompanying drawings, wherein.

NOTATION AND NOMENCLATURE

Figure 1:
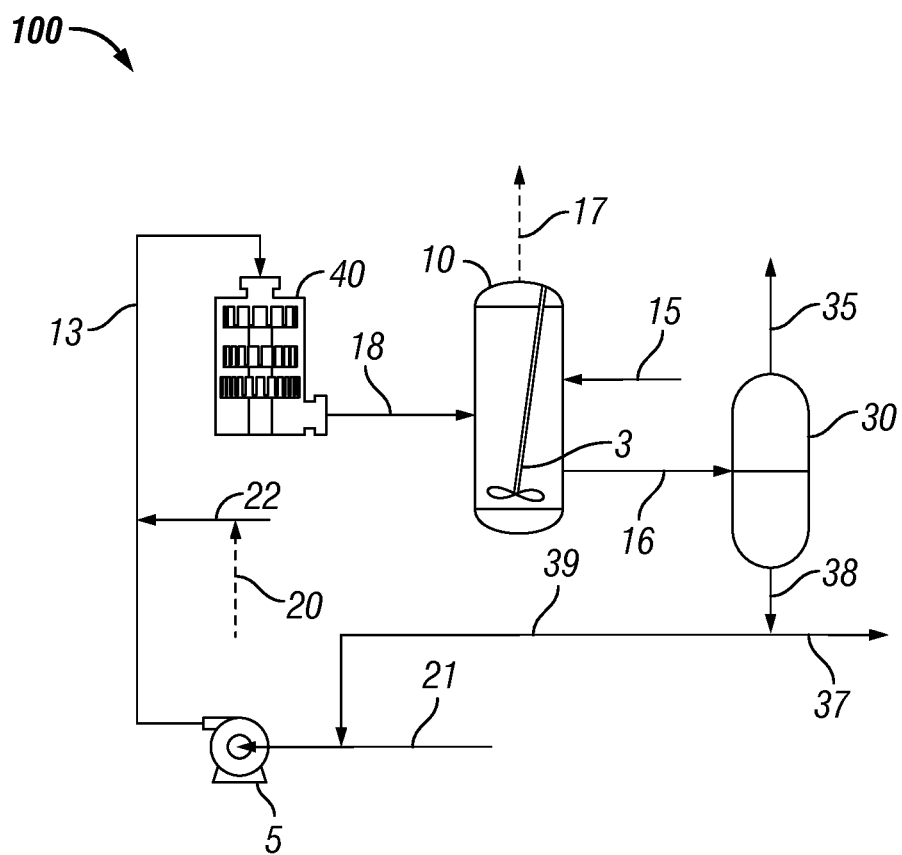
FIG. 1 is a process flow diagram of an alkylation system according to an embodiment of the present disclosure comprising external high shear dispersing.

As used herein, the term "dispersion" refers to a liquefied mixture that contains at least two distinguishable substances (or "phases") that will not readily mix and dissolve together. As used herein, a "dispersion" comprises a "continuous" phase (or "matrix"), which holds therein discontinuous droplets, bubbles, and/or particles of the other phase or substance.

The term dispersion may thus refer to foams comprising gas bubbles suspended in a liquid continuous phase, emulsions in which droplets of a first liquid are dispersed throughout a continuous phase comprising a second liquid with which the first liquid is immiscible, and continuous liquid phases throughout which solid particles are distributed. As used herein, the term "dispersion" encompasses continuous liquid phases throughout which gas bubbles are distributed, continuous liquid phases throughout which solid particles (e.g., solid catalyst) are distributed, continuous phases of a first liquid throughout which droplets of a second liquid that is substantially insoluble in the continuous phase are distributed, and liquid phases throughout which any one or a combination of solid particles, immiscible liquid droplets, and gas bubbles are distributed. Hence, a dispersion can exist as a homogeneous mixture in some cases (e.g., liquid/liquid phase), or as a heterogeneous mixture (e.g., gas/liquid, solid/liquid, or gas/solid/liquid), depending on the nature of the materials selected for combination.

DETAILED DESCRIPTION

Overview

The present processes and systems for alkylation via liquid phase reaction of isoparaffins and olefins with acid catalyst comprises an external high shear mechanical device to provide rapid contact and mixing of the chemical ingredients in a controlled environment in a high shear mixing device, which may also serve as a reactor. The high shear device reduces the mass transfer limitations on the reaction and thus increases the overall reaction rate.

The alkylation of isoparaffin (e.g., isobutane) with low molecular weight alkenes (e.g., propylene and butylene) in the presence of catalyst (e.g., strong acid catalyst such as sulfuric acid or hydrofluoric acid) is a multiphase reaction. The two phases separate spontaneously without agitation. The presently disclosed method and system whereby the acid phase is intimately mixed with the hydrocarbon phase to form an emulsion enhances contact surface between the reaction components, thus enhancing the reaction. The disclosed high shear system and method may be incorporated into conventional alkylation process, thereby enhancing yield of alkylated isoparaffin, reducing catalyst requirements (and thereby also minimizing downstream catalyst removal), and/or permitting the use of decreased amounts of excess isoparaffin in the feed.

The rate of chemical reactions involving liquids, gases and solids depend on time of contact, temperature, and pressure. In cases where it is desirable to react two or more raw materials of different phases (e.g. solid and liquid; liquid and gas; solid, liquid and gas), one of the limiting factors controlling the rate of reaction involves the contact time of the reactants. In the case of heterogeneously catalyzed reactions there is the additional rate limiting factor of having the reacted products removed from the surface of the catalyst to permit the catalyst to catalyze further reactants. Contact time for the reactants and/or catalyst is often controlled by mixing which provides contact with two or more reactants involved in a chemical reaction. Homogeneous reactions (e.g., liquid-liquid phase) may also benefit from high shear mixing, as disclosed herein, by at least providing uniform temperature distribution within the reactor and minimizing potential side reactions. Accordingly, in some embodiments, a high shear process as described herein promotes homogeneous reaction(s).

A reactor assembly that comprises an external high shear device or mixer as described herein makes possible decreased mass transfer limitations and thereby allows the reaction to more closely approach kinetic limitations. When reaction rates are accelerated, residence times may be decreased, thereby increasing obtainable throughput. Product yield may be increased as a result of the high shear system and process. Alternatively, if the alkylate yield of an existing process is acceptable, decreasing the required residence time by incorporation of suitable high shear may allow for the use of lower temperatures and/or pressures, increased alkylate product per unit of catalyst consumed, and/or the use of a reduced excess of olefin than conventional processes.

Furthermore, without wishing to be limited by theory, it is believed that the high shear conditions provided by a reactor assembly that comprises an external high shear device or mixer as described herein may permit alkylation at global operating conditions under which reaction may not conventionally be expected to occur to any significant extent. Although the discussion of the system and method will be made with reference to alkylation of isoparaffins, it is to be understood that the disclosed system and method may also be applicable to other alkylations and acylations.

System for Alkylation. A high shear alkylation system will now be described in relation to FIG. 1, which is a process flow diagram of an embodiment of a high shear system 100 for alkylation of feedstock comprising isoparaffin with low molecular weight alkene (e.g., propene and butane) by liquid phase reaction in the presence of a strong acid catalyst (e.g., sulfuric acid or hydrofluoric acid). It should be noted that FIG. 1 is a simplified process diagram and many pieces of process equipment, such as separators, heaters and compressors, have been omitted for clarity. The basic components of a representative system include external high shear mixing device (HSD) 40, vessel 10, and pump 5. As shown in FIG. 1, high shear device 40 is located external to vessel/reactor 10. Each of these components is further described in more detail below. Line 21 is connected to pump 5 for introducing a liquid stream comprising liquid acid catalyst. Line 13 connects pump 5 to HSD 40, and line 18 connects HSD 40 to vessel 10. Line 22 may be connected to line 13 for introducing a feedstream comprising isoparaffin to be alkylated and alkene. Alternatively, in embodiments, line 22 may be connected to an inlet of HSD 40 or introduced into line 21. Line 17 may be connected to vessel 10 for removal of vent gas containing unreacted hydrocarbon vapor and any other reaction gases. Additional components or process steps may be incorporated between vessel 10 and HSD 40, or ahead of pump 5 or HSD 40, if desired, as will become apparent upon reading the description of the high shear alkylation process described hereinbelow.

For example, line 38 may be connected to line 13 or line 21 from a downstream location (e.g., line 39 from settler 30), to provide for multi-pass operation, if desired.

High Shear Mixing Device. External high shear mixing device (HSD) 40, also sometimes referred to as a high shear device or high shear mixing device, is configured for receiving an inlet stream, via line 13, comprising hydrocarbon feed and concentrated acid catalyst. Alternatively, HSD 40 may be configured for receiving the liquid catalyst and the liquid hydrocarbon via separate inlet lines (not shown). Although only one high shear device is shown in FIG. 1, it should be understood that some embodiments of the system may have two or more high shear mixing devices arranged either in series or parallel flow. HSD 40 is a mechanical device that utilizes one or more generator comprising a rotor/stator combination, each of which has a gap between the stator and rotor. The gap between the rotor and the stator in each generator set may be fixed or may be adjustable. HSD 40 is configured in such a way that it is capable of producing an emulsion containing submicron (i.e., less than one micron in diameter) and/or micron-sized particles containing hydrocarbon dispersed in a continuous acid phase flowing through the high shear device. The high shear device comprises an enclosure or housing so that the pressure and temperature of the reaction mixture may be controlled.

High shear mixing devices are generally divided into three general classes, based upon their ability to mix fluids. Mixing is the process of reducing the size of particles or inhomogeneous species within the fluid. One metric for the degree or thoroughness of mixing is the energy density per unit volume that the mixing device generates to disrupt the fluid particles. The classes are distinguished based on delivered energy densities. Three classes of industrial mixers having sufficient energy density to consistently produce mixtures or emulsions with droplet sizes in the range of submicron to 50 microns include homogenization valve systems, colloid mills and high speed mixers. In the first class of high energy devices, referred to as homogenization valve systems, fluid to be processed is pumped under very high pressure through a narrow-gap valve into a lower pressure environment. The pressure gradients across the valve and the resulting turbulence and cavitation act to break-up any particles in the fluid. These valve systems are most commonly used in milk homogenization and can yield average droplet (globule) sizes in the submicron to about 1 micron range.

At the opposite end of the energy density spectrum is the third class of devices referred to as low energy devices. These systems usually have paddles or fluid rotors that turn at high speed in a reservoir of fluid to be processed, which in many of the more common applications is a food product. These low energy systems are customarily used when average particle sizes of greater than 20 microns are acceptable in the processed fluid.

Between the low energy devices and homogenization valve systems, in terms of the mixing energy density delivered to the fluid, are colloid mills and other high speed rotor-stator devices, which are classified as intermediate energy devices. A typical colloid mill configuration includes a conical or disk rotor that is separated from a complementary, liquid-cooled stator by a closely-controlled rotor-stator gap, which is commonly between 0.0254 mm to 10.16 mm (0.001-0.40 inch). Rotors are usually driven by an electric motor through a direct drive or belt mechanism. As the rotor rotates at high rates, it pumps fluid between the outer surface of the rotor and the inner surface of the stator, and shear forces generated in the gap process the fluid. Many colloid mills with proper adjustment achieve average particle sizes of 0.1-25 microns in the processed fluid. These capabilities render colloid mills appropriate for a variety of applications including colloid and oil/water-based emulsion processing such as that required for cosmetics, mayonnaise, or silicone/silver amalgam formation, to roofing-tar mixing.

Tip speed is the circumferential distance traveled by the tip of the rotor per unit of time. Tip speed is thus a function of the rotor diameter and the rotational frequency. Tip speed (in meters per minute, for example) may be calculated by multiplying the circumferential distance transcribed by the rotor tip, $2\pi R$, where R is the radius of the rotor (meters, for example) times the frequency of revolution (for example revolutions per minute, rpm). A colloid mill, for example, may have a tip speed in excess of 22.9 m/s (4500 ft/min) and may exceed 40 m/s (7900 ft/min) For the purpose of this disclosure, the term 'high shear' refers to mechanical rotor stator devices (e.g., colloid mills or rotor-stator dispersers) that are capable of tip speeds in excess of 5.1 m/s. (1000 ft/min) and require an external mechanically driven power device to drive energy into the stream of products to be reacted. For example, in HSD 40, a tip speed in excess of 22.9 m/s (4500 ft/min) is achievable, and may exceed 40 m/s (7900 ft/min). In some embodiments, HSD 40 is capable of delivering at least 300 L/h at a tip speed of at least 22.9 m/s (4500 ft/min) The power consumption may be about 1.5 kW.

HSD 40 combines high tip speed with a very small shear gap to produce significant shear on the material being processed. The amount of shear will be dependent on the viscosity of the fluid. Accordingly, a local region of elevated pressure and temperature is created at the tip of the rotor during operation of the high shear device. In some cases the locally elevated pressure is about 1034.2 MPa (150,000 psi). In some cases the locally elevated temperature is about 500° C. In some cases, these local pressure and temperature elevations may persist for nano or pico seconds.

An approximation of energy input into the fluid (kW/L/min) can be estimated by measuring the motor energy (kW) and fluid output (L/min) As mentioned above, tip speed is the velocity (ft/min or m/s) associated with the end of the one or more revolving elements that is creating the mechanical force applied to the reactants. In embodiments, the energy expenditure of HSD 40 is greater than 1000 W/m$^3$. In embodiments, the energy expenditure of HSD 40 is in the range of from about 3000 W/m$^3$ to about 7500 W/m$^3$.

The shear rate is the tip speed divided by the shear gap width (minimal clearance between the rotor and stator). The shear rate generated in HSD 40 may be in the greater than 20,000 s$^{-1}$. In some embodiments the shear rate is at least 40,000 s$^{-1}$. In some embodiments the shear rate is at least 100,000 s$^{-1}$. In some embodiments the shear rate is at least 500,000 s$^{-1}$. In some embodiments the shear rate is at least 1,000,000 s$^{-1}$. In some embodiments the shear rate is at least 1,600,000 s$^{-1}$. In embodiments, the shear rate generated by HSD 40 is in the range of from 20,000 s$^{-1}$ to 100,000 s$^{-1}$. For example, in one application the rotor tip speed is about 40 m/s (7900 ft/min) and the shear gap width is 0.0254 mm (0.001 inch), producing a shear rate of 1,600,000 s$^{-1}$. In another application the rotor tip speed is about 22.9 m/s (4500 ft/min) and the shear gap width is 0.0254 mm (0.001 inch), producing a shear rate of about 901,600 s$^{-1}$.

HSD 40 is capable of highly emulsifying hydrocarbon into a main liquid phase comprising acid with which the hydrocarbon would normally be immiscible, at conditions such that at least a portion of the small olefins and isoparaffins are converted into larger isoparaffins with a high octane number. Although not discussed in detail herein, it is understood that, in embodiments, a viscous acid phase may be utilized, and, in such cases, HSD 40 may be used to form an emulsion comprising viscous acid catalyst dispersed in a continuous hydrocarbon phase. Thus, in embodiments, the continuous phase comprises acid catalyst. In alternative embodiments, the continuous phase comprises hydrocarbon.

In embodiments, the emulsion further comprises a solid particulate catalyst. In some embodiments, HSD 40 comprises a colloid mill. Suitable colloidal mills are manufactured by IKA® Works, Inc. Wilmington, N.C. and APV North America, Inc. Wilmington, Mass., for example. In some instances, HSD 40 comprises the Dispax Reactor® of IKA® Works, Inc.

The high shear device comprises at least one revolving element that creates the mechanical force applied to the reactants. The high shear device comprises at least one stator and at least one rotor separated by a clearance. For example, the rotors may be conical or disk shaped and may be separated from a complementarily-shaped stator. In embodiments, both the rotor and stator comprise a plurality of circumferentially-spaced teeth. In some embodiments, the stator(s) are adjustable to obtain the desired shear gap between the rotor and the stator of each generator (rotor/stator set). Grooves between the teeth of the rotor and/or stator may alternate direction in alternate stages for increased turbulence. Each generator may be driven by any suitable drive system configured for providing the necessary rotation.

In some embodiments, the minimum clearance (shear gap width) between the stator and the rotor is in the range of from about 0.0254 mm (0.001 inch) to about 3.175 mm (0.125 inch). In certain embodiments, the minimum clearance (shear gap width) between the stator and rotor is about 1.52 mm (0.060 inch). In certain configurations, the minimum clearance (shear gap) between the rotor and stator is at least 1.78 mm (0.07 inch). The shear rate produced by the high shear device may vary with longitudinal position along the flow pathway. In some embodiments, the rotor is set to rotate at a speed commensurate with the diameter of the rotor and the desired tip speed. In some embodiments, the high shear device has a fixed clearance (shear gap width) between the stator and rotor. Alternatively, the high shear device has adjustable clearance (shear gap width).

In some embodiments, HSD 40 comprises a single stage dispersing chamber (i.e., a single rotor/stator combination, a single generator). In some embodiments, high shear device 40 is a multiple stage inline disperser and comprises a plurality of generators. In certain embodiments, HSD 40 comprises at least two generators. In other embodiments, high shear device 40 comprises at least 3 high shear generators. In some embodiments, high shear device 40 is a multistage mixer whereby the shear rate (which, as mentioned above, varies proportionately with tip speed and inversely with rotor/stator gap width) varies with longitudinal position along the flow pathway, as further described herein below.

In some embodiments, each stage of the external high shear device has interchangeable mixing tools, offering flexibility. For example, the DR 2000/4 Dispax Reactor® of IKA® Works, Inc. Wilmington, N.C. and APV North America, Inc. Wilmington, Mass., comprises a three stage dispersing module. This module may comprise up to three rotor/stator combinations (generators), with choice of fine, medium, coarse, and super-fine for each stage. This allows for creation of emulsions having a narrow distribution of the desired droplet size (e.g., hydrocarbon droplets). In some embodiments, each of the stages is operated with super-fine generator. In some embodiments, at least one of the generator sets has a rotor/stator minimum clearance (shear gap width) of greater than about 5.08 mm (0.20 inch). In alternative embodiments, at least one of the generator sets has a minimum rotor/stator clearance of greater than about 1.78 mm (0.07 inch).

Figure 2:
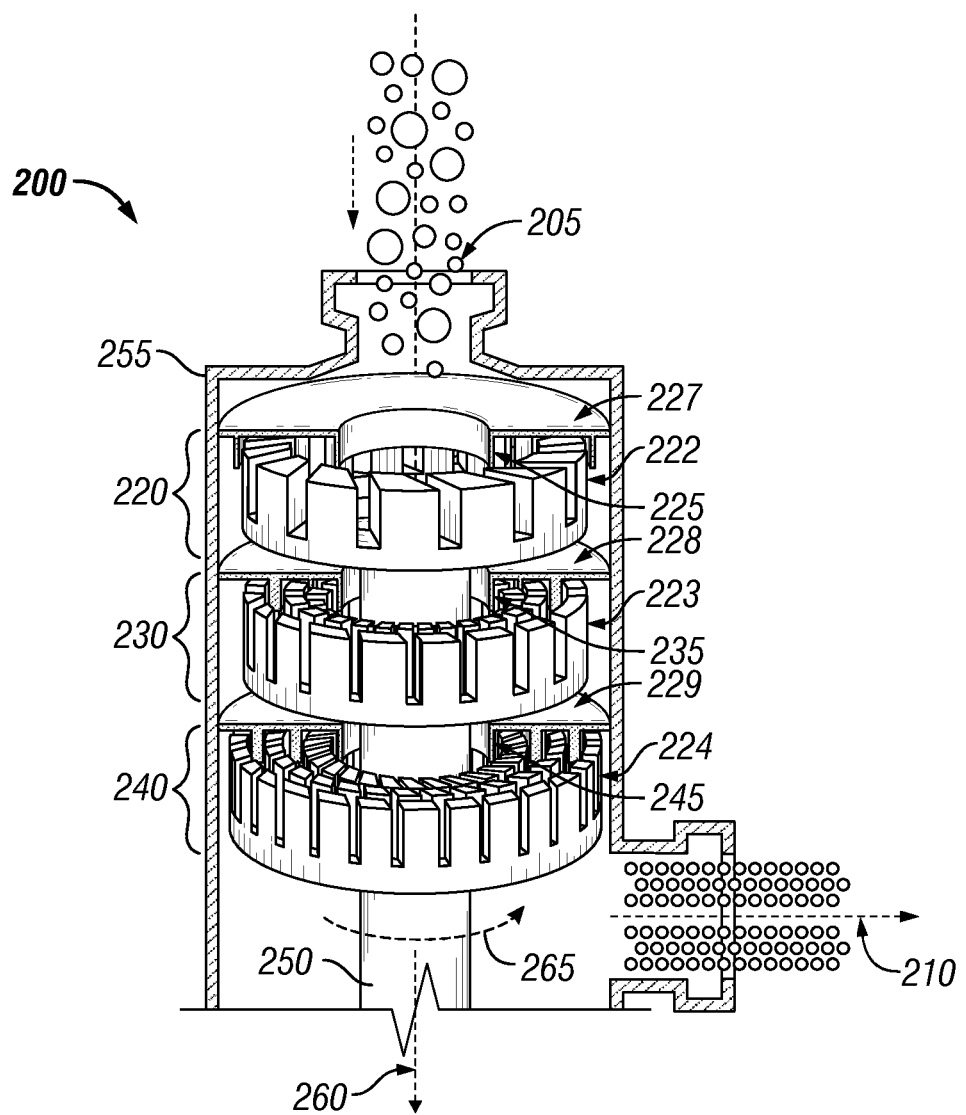
FIG. 2 is a longitudinal cross-section view of a multi-stage high shear device, as employed in an embodiment of the system.

Referring now to FIG. 2, there is presented a longitudinal cross-section of a suitable high shear device 200. High shear device 200 of FIG. 2 is a dispersing device comprising three stages or rotor-stator combinations. High shear device 200 is a dispersing device comprising three stages or rotor-stator combinations, 220, 230, and 240. The rotor-stator combinations may be known as generators 220, 230, 240 or stages without limitation. Three rotor/stator sets or generators 220, 230, and 240 are aligned in series along drive shaft 250.

First generator 220 comprises rotor 222 and stator 227. Second generator 230 comprises rotor 223, and stator 228. Third generator 240 comprises rotor 224 and stator 229. For each generator the rotor is rotatably driven by input 250 and rotates about axis 260 as indicated by arrow 265. The direction of rotation may be opposite that shown by arrow 265 (e.g., clockwise or counterclockwise about axis of rotation 260). Stators 227, 228, and 229 are fixably coupled to the wall 255 of high shear device 200.

As mentioned hereinabove, each generator has a shear gap width which is the minimum distance between the rotor and the stator. In the embodiment of FIG. 2, first generator 220 comprises a first shear gap 225; second generator 230 comprises a second shear gap 235; and third generator 240 comprises a third shear gap 245. In embodiments, shear gaps 225, 235, 245 have widths in the range of from about 0.025 mm to about 10.0 mm. Alternatively, the process comprises utilization of a high shear device 200 wherein the gaps 225, 235, 245 have a width in the range of from about 0.5 mm to about 2.5 mm. In certain instances the shear gap width is maintained at about 1.5 mm. Alternatively, the width of shear gaps 225, 235, 245 are different for generators 220, 230, 240. In certain instances, the width of shear gap 225 of first generator 220 is greater than the width of shear gap 235 of second generator 230, which is in turn greater than the width of shear gap 245 of third generator 240. As mentioned above, the generators of each stage may be interchangeable, offering flexibility. High shear device 200 may be configured so that the shear rate will increase stepwise longitudinally along the direction of the flow 260.

Generators 220, 230, and 240 may comprise a coarse, medium, fine, and super-fine characterization. Rotors 222, 223, and 224 and stators 227, 228, and 229 may be toothed designs. Each generator may comprise two or more sets of rotor-stator teeth. In embodiments, rotors 222, 223, and 224 comprise more than 10 rotor teeth circumferentially spaced about the circumference of each rotor. In embodiments, stators 227, 228, and 229 comprise more than ten stator teeth circumferentially spaced about the circumference of each stator. In embodiments, the inner diameter of the rotor is about 12 cm. In embodiments, the diameter of the rotor is about 6 cm. In embodiments, the outer diameter of the stator is about 15 cm. In embodiments, the diameter of the stator is about 6.4 cm. In some embodiments the rotors are 60 mm and the stators are 64 mm in diameter, providing a clearance of about 4 mm. In certain embodiments, each of three stages is operated with a super-fine generator, comprising a shear gap of between about 0.025 mm and about 4 mm. For applications in which solid particles are to be sent through high shear device 40, the appropriate shear gap width (minimum clearance between rotor and stator) may be selected for an appropriate reduction in particle size and increase in particle surface area. In embodiments, this may be beneficial for increasing catalyst surface area by shearing and dispersing the particles.

High shear device 200 is configured for receiving from line 13 a reactant stream at inlet 205. The reaction mixture comprises acid catalyst as the dispersible phase and hydrocarbon liquid as the continuous phase. The feed stream may further comprise a particulate solid catalyst component. Feed stream entering inlet 205 is pumped serially through generators 220, 230, and then 240, such that product emulsion is formed. Product emulsion exits high shear device 200 via outlet 210 (and line 18 of FIG. 1). The rotors 222, 223, 224 of each generator rotate at high speed relative to the fixed stators 227, 228, 229, providing a high shear rate. The rotation of the rotors pumps fluid, such as the feed stream entering inlet 205, outwardly through the shear gaps (and, if present, through the spaces between the rotor teeth and the spaces between the stator teeth), creating a localized high shear condition. High shear forces exerted on fluid in shear gaps 225, 235, and 245 (and, when present, in the gaps between the rotor teeth and the stator teeth) through which fluid flows process the fluid and create product emulsion. Product emulsion exits high shear device 200 via high shear outlet 210 (and line 18 of FIG. 1).

The product emulsion comprising droplets, in a continuous liquid phase may be referred to as an dispersion or an emulsion herein. The product emulsion has an average droplet size less than about 5 µm. In embodiments, HSD 40 produces an emulsion having a mean droplet size of less than about 1.5 µm. In embodiments, HSD 40 produces an emulsion having a mean droplet size of less than 1 µm; preferably the droplets are sub-micron in diameter. In certain instances, the average droplet size is from about 0.1 µm to about 1.0 µm. In embodiments, HSD 40 produces an emulsion having a mean droplet size of less than 400 nm. In embodiments, HSD 40 produces an emulsion having a mean droplet size of less than 100 nm. High shear device 200 produces an emulsion comprising dispersed droplets capable of remaining dispersed at atmospheric pressure for at least about 10 minutes or at least about 15 minutes.

In certain instances, high shear device 200 comprises a Dispax Reactor® of IKA® Works, Inc. Wilmington, N.C. and APV North America, Inc. Wilmington, Mass. Several models are available having various inlet/outlet connections, horsepower, tip speeds, output rpm, and flow rate. Selection of the high shear device will depend on throughput requirements and desired droplet or globule size in the emulsion in line 18 (FIG. 1) exiting outlet 210 of high shear device 200. IKA® model DR 2000/4, for example, comprises a belt drive, 4M generator, PTFE sealing ring, inlet flange 25.4 mm (1 inch) sanitary clamp, outlet flange 19 mm (¾ inch) sanitary clamp, 2HP power, output speed of 7900 rpm, flow capacity (water) approximately 300-700 L/h (depending on generator), a tip speed of from 9.4-41 m/s (1850 ft/min to 8070 ft/min).

Vessel. The emulsion in line 18 enters reactor 10 wherein alkylation continues. Vessel or reactor 10 is any type of vessel in which the multiphase alkylation reaction can be propagated. Vessel 10 may be any suitable vessel, for example, a continuous stirred tank reactor such as that typically employed in sulfuric acid alkylation or a tubular riser-type reactor such as is typically used for hydrofluoric acid alkylation. Vessel 10 may be, for instance, a continuous or semi-continuous stirred tank reactor, or one or more batch reactors may be employed in series or in parallel. In some applications vessel 10 may be a tower reactor, and in others a tubular reactor or multi-tubular reactor. One or more line 15 may be connected to vessel 10 for introducing the acid catalyst, or for injecting water, or other material (e.g., a solid catalyst).

Alkylation reactions will occur whenever suitable time, temperature and pressure conditions exist. In this sense alkylation could occur at any point in the flow diagram of FIG. 1 if temperature and pressure conditions are suitable.

Vessel 10 may include one or more of the following components: stirring system, temperature control capabilities, pressure measurement instrumentation, temperature measurement instrumentation, one or more injection points, and level regulator (not shown), as are known in the art of reaction vessel design. For example, a stirring system may include a motor driven mixer 3, as indicated in FIG. 1. A temperature control apparatus may comprise, for example, a heat exchanger. Alternatively, as much of the alkylation may occur within HSD 40 in some embodiments, vessel 10 may serve primarily as a storage vessel in some cases. Although generally less desired, in some applications vessel 10 may be omitted, particularly if multiple high shear devices/reactors are employed in series, as further described below.

Line 16 is connected to vessel 10 for withdrawal or removal of reaction product containing alkylate. In some embodiments, a separating tank 30 may be connected to vessel 10 by line 16, for separation of hydrocarbon from acid catalyst, which may be recycled to HSD 40, if desired. Line 17 may be connected to vessel 10 for removal of vent gas. In embodiments, vessel 10 comprises a plurality of reactor product lines 16.

Heat Transfer Devices. In addition to the above-mentioned heating/cooling capabilities of vessel 10, other external or internal heat transfer devices for heating or cooling a process stream are also contemplated in variations of the embodiments illustrated in FIG. 1. For example, if the reaction is exothermic, reaction heat may be removed from vessel 10 via any method known to one skilled in the art. The use of external heating and/or cooling heat transfer devices is also contemplated. Some suitable locations for one or more such heat transfer devices are between pump 5 and HSD 40, between HSD 40 and vessel 10, and between vessel 10 and pump 5 when system 100 is operated in multi-pass mode. Some non-limiting examples of such heat transfer devices are shell, tube, plate, and coil heat exchangers, as are known in the art.

Pumps. Pump 5 is configured for either continuous or semi-continuous operation, and may be any suitable pumping device that is capable of providing greater than 202.65 kPa (2 atm) pressure, preferably greater than 303.975 kPa (3 atm) pressure, to allow controlled flow through HSD 40 and system 100. For example, a Roper Type 1 gear pump, Roper Pump Company (Commerce Ga.) Dayton Pressure Booster Pump Model 2P372E, Dayton Electric Co (Niles, Ill.) is one suitable pump. Preferably, all contact parts of the pump comprise stainless steel, or, when corrosive substances such as concentrated acid will be pumped, the contact surfaces may be gold plated. In some embodiments of the system, pump 5 is capable of pressures greater than about 2026.5 kPa (20 atm). In addition to pump 5, one or more additional, high pressure pump (not shown) may be included in the system illustrated in FIG. 1. For example, a booster pump, which may be similar to pump 5, may be included between HSD 40 and vessel 10 for boosting the pressure into vessel 10. As another example, a supplemental feed pump, which may be similar to pump 5, may be included for introducing the strong acid, water, or additional reactants or a solid catalyst into vessel 10. Although not shown in FIG. 1, an outlet line may connect vessel 10 to line 21 for introducing acid catalyst into HSD 40 via pump 5 and line 13.

Alkylation Process. Operation of high shear alkylation system 100 will now be discussed with reference to FIG. 1. In operation for the alkylation of hydrocarbon streams comprising isoparaffin, a dispersible hydrocarbon feed stream is introduced into system 100 via line 22, and combined in line 13 with a liquid stream in line 21 comprising acid catalyst.

Hydrocarbon feedstream introduced in line 22 comprises at least an olefin and a paraffin to be alkylated. In embodiments, the isoparaffin reactant used in the present alkylation process contains from about 4 to about 8 carbon atoms. Representative examples of such isoparaffins include isobutane, isopentane, 3-methylhexane, 2-methylhexane, 2,3-dimethylbutane and 2,4-dimethylhexane. In embodiments, the isoparaffin is isobutene. The olefin component of the feedstock includes at least one olefin having from 2 to 12 carbon atoms. Representative examples of such olefins include butene-2, isobutylene, butene-1, propylene, ethylene, hexene, octene, and heptene, for example. The most preferred olefins may be C3 and C4 olefins, for example, propylene, butene-1, butene-2, isobutylene, or a mixture of two or more of these olefins. In embodiments, the hydrocarbon feedstream in line 22 comprises an olefin selected from propylene, butylenes, pentylenes, and combinations thereof. In embodiments, hydrocarbon feedstream in line 22 comes from a fluidized catalytic cracking unit.

The ratio of isoparaffin to olefin is conventionally kept high during alkylation of isoparaffins to prevent/minimize side reactions that may reduce the octane rating of the product. In embodiments, the overall molar ratio of isoparaffin to olefin in the hydrocarbon feed is in the range of from 1:1 and 100:1, preferably between about 5:1 and about 20:1. Use of the disclosed high shear system and method may permit alkylation at lower isoparaffin to olefin ratio than conventional.

In embodiments, the catalyst is a liquid catalyst. In embodiments, the catalyst is a solid catalyst. In embodiments, the catalyst is a combination of liquid and solid phase catalyst. In embodiments, dispersible reactant in line 21 comprises liquid acid catalyst.

In embodiments, dispersible catalyst in line 21 comprises a Bronsted acid. In embodiments, catalyst line 21 comprises a Bronsted acid selected from hydrofluoric acid and sulfuric acid. As both hydrofluoric and sulfuric acid catalysts are gradually depleted in continuous alkylation, fresh acid may be continuously introduced into line 21 to maintain acid strength, reaction rate, and the resulting alkylate quality. Alkylate quality is affected by acid strength, and fresh acid makeup and/or regeneration rate may be controlled together with other process variables such as temperature and space velocity, to meet a required alkylate quality specification. Typically, more concentrated acid catalysts maximize yield of isoparaffins and suppress undesirable olefin oligomerization side reactions. In embodiments, catalyst line 21 comprises a Lewis acid. The Lewis acid may comprise $BF_3$ or $BF_3:H_3PO_4$ adducts.

Acid strength in these liquid acid catalyzed alkylation processes is preferably maintained at 88 to 94 weight percent by the continuous addition of fresh acid in line 21 and the continuous withdrawal of spent acid. In embodiments, spent acid is removed from high shear system 100 via spent acid line 38, a portion of which may be recycled to high shear device 40 via, for example, introduction into acid line 21 via acid recycle line 39. Acid recycled to HSD 40 via line 21 may undergo further treatment prior to reintroduction into HSD 40. In embodiments, fresh catalyst enters high shear system 100 upstream of high shear device 40. In embodiments, fresh acid catalyst is introduced to high shear alkylation system 100 via inlet line 15. In embodiments, spend acid is removed from high shear system 100 via spent acid line 37.

In embodiments, high shear system 100 comprises a suitable solid catalyst as disclosed in the art. In embodiments, the alkylation reaction carried out by high shear process 100 is a heterogeneous catalytic reaction involving a solid catalyst. In embodiments wherein a solid catalyst is utilized, reactor 10 may comprise, for example, a fixed or a slurry bed. In embodiments, reactor 10 comprises a solid catalyst. For example, in embodiments, the catalyst comprises one or more transitional aluminas which are treated with at least one Lewis acid, preferably $BF_3$. The process may also utilize an amount of free Lewis acid and to produce high octane alkylate. In embodiments, the solid catalyst comprises a large pore zeolite ZSM-4, ZSM-20, ZSM-3, ZSM-18, zeolite Beta, faujasite, mordenite, zeolite Y and the rare earth metal-containing forms of zeolite Y, and a Lewis acid such as $BF_3$, $SbF_5$, or $AlCl_3$. In embodiments, the catalyst comprises Lewis acid and a solid component comprising a layered silicate and pillars of an oxide separating the layers of the silicate. A suitable solid catalyst may include acidic zeolites, alumina, silica-alumina, silica, boron oxides, phosphorus oxides, titanium oxide, zirconium oxide, chromia, zinc oxide, magnesia, calcium oxide, silica-alumina-zirconia, chromia-alumina, alumina-boria, silica-zirconia, aluminum phosphate molecular sieves, silicoaluminophosphate molecular sieves, solid polymeric ion exchange resins, tetravalent metal phosphonates with pendent acid groups, sulfated metal oxides (such as alumina), and the like. These catalysts may be treated with or complexed with Lewis acids. They are all acidic in their functionality as hydrocarbon conversion catalysts.

If a solid catalyst is used to promote the alkylation reaction in some embodiments, it may be introduced into vessel 10 via line 15, as an aqueous or nonaqueous slurry or stream. Alternatively, or additionally, catalyst may be added elsewhere in the system 1. For example, catalyst slurry may be injected into line 21. In some embodiments, the catalyst is added continuously to vessel 10 via line 15. Without wishing to be limited by theory, it is believed that sub-micron particles or bubbles dispersed in a liquid undergo movement primarily through Brownian motion effects. The droplets in the product emulsion created by HSD 40 may have greater mobility through boundary layers of solid catalyst particles, thereby facilitating and accelerating the catalytic reaction through enhanced transport of reactants.

A stream of concentrated liquid acid is introduced into line 21, and is pumped through line 13 into HSD 40. In line 13, the acid mixture is combined with a liquid hydrocarbon introduced into line 13 via line 22. Alternatively, the hydrocarbon may be fed directly into HSD 40, or combined with acid upstream of pump 5 rather than being combined with the acid in line 13. Pump 5 is operated to pump the acid through line 21, and to build pressure and feed HSD 40, providing a controlled flow throughout high shear mixer (HSD) 40 and system 100. In some embodiments, pump 5 increases the pressure of the HSD inlet stream to greater than 345 kPa (50 psig). In some embodiments, pump 5 increases the pressure of the stream to greater than 3447 kPa (500 psig). In some embodiments, pump 5 increases the pressure of the stream to greater than 202.65 kPa (29 psig) or greater than about 303.975 kPa (44 psig). In this way, high shear system 100 may combine high shear with pressure to enhance reactant intimate mixing of the reaction mixture.

In this manner, external high shear device 40 produces an emulsion of dispersible reactant from line 22 within continuous phase introduced via line 21.

In contrast to other systems, the presently disclosed high shear system 100 comprises an enclosed external high shear mixing device 40 to create an emulsion (and/or submicron-sized globules) of hydrocarbon in acid catalyst (or acid catalyst in hydrocarbon). As discussed in detail hereinabove, external high shear device 40 is a mechanical device that utilizes, for example, a stator rotor mixing head with a fixed gap between the stator and rotor. Dispersible catalyst and liquid hydrocarbons are introduced separately or as a mixed stream into HSD 40. Mixing results in an emulsion of dispersible catalyst in micron or sub micron droplet sizes. Therefore, high shear mixer outlet line 18 comprises an emulsion of micron and/or submicron-sized globules, as discussed hereinabove.

In some embodiments, hydrocarbon feed is continuously fed into line 13 to form the feed stream to HSD 40. Water may also be introduced with the acid, or it may be introduced independently. The actual ratio of raw materials depends on the desired selectivity and operating temperatures and pressures.

After pumping, the hydrocarbon and acid reactants are mixed within HSD 40, which serves to create a fine dispersion or emulsion of the hydrocarbon in the concentrated acid mixture. In HSD 40, the hydrocarbon and the concentrated acid catalyst are highly dispersed such that an emulsion is formed. The emulsion may be a nonaemulsion. An emulsion or nanoemulsion is sometimes also referred to herein as a "dispersion." For the purposes of this disclosure, a nanoemulsion is an emulsion of immiscible liquid phases in which the sizes of the droplets (globules) in the dispersed phase are less than 1000 nanometers (i.e., <1 micron). For example, disperser IKA® model DR 2000/4, a high shear, three stage dispersing device configured with three rotors in combination with stators, aligned in series, is used to create the emulsion of hydrocarbon in the liquid medium comprising the concentrated acid catalyst. The rotor/stator sets may be configured as illustrated in FIG. 2, for example. The combined reactants enter the high shear mixer via line 13 and enter a first stage rotor/stator combination having circumferentially spaced first stage shear openings. The coarse emulsion exiting the first stage enters the second rotor/stator stage, having second stage shear openings. The reduced droplet-size emulsion emerging from the second stage enters the third stage rotor/stator combination having third stage shear openings. The emulsion exits the high shear mixer via line 18. In some embodiments, the shear rate increases stepwise longitudinally along the direction of the flow. For example, in some embodiments, the shear rate in the first rotor/stator stage is greater than the shear rate in subsequent stage(s). In other embodiments, the shear rate is substantially constant along the direction of the flow, with the stage or stages being the same. If the high shear mixer includes a PTFE seal, for example, the seal may be cooled using any suitable technique that is known in the art. For example, the reactant stream flowing in line 13 may be used to cool the seal and in so doing be preheated as desired prior to entering the high shear mixer.

The rotor of HSD 40 is set to rotate at a speed commensurate with the diameter of the rotor and the desired tip speed. As described above, the high shear mixer (e.g., colloid mill) has either a fixed clearance between the stator and rotor or has adjustable clearance. HSD 40 serves to intimately mix the hydrocarbon and the concentrated acid. In some embodiments of the process, the transport resistance of the reactants is reduced by operation of the high shear mixer such that the velocity of the reaction is increased by greater than a factor of about 5. In some embodiments, the velocity of the reaction is increased by at least a factor of 10. In some embodiments, the velocity is increased by a factor in the range of about 10 to about 100 fold. In some embodiments, HSD 40 delivers at least 300 L/h with a power consumption of 1.5 kW at a nominal tip speed of at least 22.9 m/s (4500 ft/min), and which may exceed 40 m/s (7900 ft/min) In some embodiments, the mixture is subjected to a shear rate greater than 20,000 $s^{-1}$.

Although measurement of instantaneous temperature and pressure at the tip of a rotating shear unit or revolving element in HSD 40 is difficult, it is estimated that the localized temperature seen by the intimately mixed reactants is in excess of 500° C. and at pressures in excess of 500 kg/cm$^2$ under cavitation conditions. The high shear mixing results in formation of an emulsion or nanoemulsion in which the dispersed hydrocarbon-containing droplets/globules are micron or submicron-sized particles (i.e., mean diameter less than one micron). In some embodiments, the resultant emulsion has an average droplet size less than about 1.5 µm. In some embodiments, the mean droplet size is in the range of about 0.4 µm to about 1.5 µm. In some embodiments, the emulsion is a nanoemulsion in which the mean diameter of the droplets is less than 1 micron in size. In some embodiments, the mean droplet size is less than about 400 nm, in the range of about 200 nm to about 400 nm, or may be about 100 nm in some cases. Accordingly, the emulsion exiting HSD 40 via line 18 comprises micron and/or submicron-sized droplets. In many embodiments, the emulsion is able to remain dispersed at atmospheric pressure for at least 15 minutes.

Once dispersed, the resulting emulsion exits HSD 40 via line 18 and feeds into vessel 10, as illustrated in FIG. 1. Alkylation of isoparaffin will occur whenever suitable time, temperature and pressure conditions exist. In this sense the reaction may occur at any point in the path between HSD 40, vessel 10 and pump 5, as shown in FIG. 1, if the temperature and pressure conditions are favorable. As a result of the intimate mixing of the reactants prior to entering vessel 10, a significant portion of the chemical reaction may take place in HSD 40. A discrete reactor is usually desirable, however, to allow for increased agitation and heating and/or cooling of the bulk reactants, and increased residence time, if applicable. Accordingly, in some embodiments, vessel 10 may be used primarily for initial introduction of catalyst and/or separation of product. Alternatively, or additionally, vessel 10 may serve as a primary reaction vessel where most or some portion of the total alkylate product is produced. In either case, the chemical reaction comprises a liquid-liquid (or liquid/liquid/solid or liquid/solid in the presence of solid catalyst) reaction in which the reactants are in the form of a very fine emulsion. The reactants (i.e., hydrocarbon and acid) comprise a two phase emulsion, or nanoemulsion.

The particular operating conditions used in the present process will depend on the specific alkylation reaction being effected. Process conditions such as temperature, pressure, space velocity and molar ratio of the reactants will effect the characteristics of the resulting alkylate, and may be adjusted within the disclosed ranges by those skilled in the art with only minimal trial and error.

The bulk or global operating temperature of the reactants is desirably maintained below their flash points. The temperature and pressure of the high shear system 100 vary depending on the feed, the type of catalyst employed, and the degree of alkylation sought in the process. Typically, the alkylation is carried out at mild temperatures. Industrial alkylation processes have historically used hydrofluoric or sulfuric acid catalysts under relatively low temperature conditions. The sulfuric acid alkylation reaction is particularly sensitive to temperature, with low temperatures being favored to minimize the side reaction of olefin polymerization.

The present alkylation process is suitably conducted at temperatures of from about −40° C. to about 500° C., preferably from below about 40° C. to avoid undesirable side reactions, and most preferably from about 0° C. to about 20° C. In embodiments, the alkylation is carried out at temperatures of from about 0° C. to about 30° C. In embodiments, the alkylation is carried out at temperatures of from about 0° C. to about 90° C. Lower reaction temperatures are preferred to maximize alkylate octane.

Operating pressure is controlled to maintain the reactants in the liquid phase, and is suitably from about 345 kPa (50 psig) to about 34.5 MPa (5000 psig), preferably from about 345 kPa (50 psig) to about 10.3 MPa (1500 psig), and more preferably from about 552 kPa (80 psig) to about 1379 kPa (200 psig). Weight hourly space velocity ranges from about 0.01 hr$^{-1}$ to about 100 hr$^{-1}$ based on total olefin feed to the reaction zone. The most preferred weight hourly space velocity varies within this range as a function of reaction temperature and feedstock composition. Weight hourly space velocity may be readily optimized to attain a desired octane specification with minimal trial and error.

The emulsion may be further processed prior to entering vessel 10, if desired. The contents of vessel 10 are stirred continuously or semi-continuously, the temperature of the reactants is controlled (e.g., using a heat exchanger), and the fluid level inside vessel 10 is regulated using standard techniques. Alkylate may be produced either continuously, semi-continuously or batch wise, as desired. Any reaction gas that is produced may exit reactor 10 via a gas line 17. This gas stream may comprise volatile products, for example. The gas removed via line 17 may be further treated and vented, or the components may be recycled, as desired.

The reaction product stream comprising non-converted liquid hydrocarbon, alkylate, and any derivatives and byproducts exits vessel 10 by way of line 16. The alkylate product may comprise a mixture of high-octane, branched paraffinic hydrocarbons. In embodiments, the alkylate comprises primarily isopentane and isooctane. In embodiments, alkylate product stream in line 16 may be suitable as a premium gasoline blendstock with antiknock and clean-burning properties. Upon removal from the reactor 10, product in line 16 may be passed to a product upgrade system for further processing, as known to those of skill in the art.

In embodiments, as shown in FIG. 1, product in line 16 is introduced to liquid-liquid separator 30. Separator 30 may be, for example, a decanter or settling tank. In separator 30, the denser liquid acid alkylation catalyst rapidly migrates to the bottom of the separator, while the alkylate product and unreacted hydrocarbon floats to the top of the settler. The liquid catalyst 38 is withdrawn from the bottom of the settler, and may be disposed via spent acid line 37 and/or introduced via line 39 into fresh catalyst line 21 for reintroduction to HSD 40. A portion of the catalyst liquid may be continuously or intermittently withdrawn from high shear system 100 via, for example, spent acid line 37, for treatment in a regeneration facility or disposal in suitable facilities (not shown).

Catalyst to be recycled may be regenerated prior to introduction into line 21. For example, in embodiments, catalyst in line 38 flows to catalyst cooler (not shown in FIG. 1) before being returned to high shear system 100. The alkylation reaction is typically exothermic, and for this reason, the catalyst may be precooled before it is returned to HSD 40 to maintain the alkylation reaction temperature within the preferred range. As noted above, temperature control in the alkylation reaction zone affects alkylate quality and is therefore an important process control consideration. A suitable cooling medium withdraws heat from the liquid acid catalyst, preferably by indirectly contacting the catalyst solution as the cooling medium flows through tubes of a shell-and-tube heat exchanger. Any suitable cooling medium known to those skilled in the art may be employed, for example, chilled water or a solution of ethylene glycol in water.

The lighter hydrocarbon phase contained in the alkylation reactor effluent charged to separator 30 readily forms a discrete hydrocarbon phase in the upper section of the separator 30. This hydrocarbon phase including not only alkylated product but also unreacted hydrocarbon as well as small amounts of acid catalyst, is withdrawn from separator 30 via product line 35. The alkylate product may be piped to a deacidification step, for example, a caustic scrubber where the hydrocarbon product contacts an aqueous caustic solution (NaOH) to remove residual acid. Because the hydrocarbon phase and the aqueous caustic phase are substantially immiscible, the two liquids are readily separated, with spent caustic and (substantially) acid-free hydrocarbon being withdrawn via separate streams from the deacidification vessel.

The catalyst-removed product 35 may be subjected to further processing and a portion of line 35 may be recycled. For example, high shear system 100 may further comprise a depropanizer (not shown in FIG. 1) from which propane may be removed for resale or use as fuel, and/or a deisobutanizer (not shown in FIG. 1) from which isobutane may be removed. A portion of recovered unconverted isobutane may be recycled to high shear device 40, for example, via recycle isoparaffin line 20. The deisobutanizer and depropanizer separators may comprise any suitable separation means known to those skilled in the art, for example, conventional multiple tray fractionation towers with reboilers and overhead condensers.

In embodiments, the acid catalyst comprises solid acid catalysts particularly zeolites or aluminas which have been treated with Lewis acids, and alkylation produces what appears to be a low level polymer or oligomer. In such embodiments, solvent extraction may be used to remove these side products.

Multiple Pass Operation. Referring still to FIG. 1, the system is configured for single pass or multipass, wherein, after introduction of the liquid reactants and commencement of the process, the output from line 16 of vessel 10 goes directly to recovery of the alkylate or to further processing. In some embodiments it may be desirable to pass the contents of line 16, or a liquid fraction thereof, through HSD 40 during a second pass. In this case, at least a portion of the product in line 16 may be returned to HSD 40, with or without intervening processing, for further emulsification and reaction. Additional acid or water may be injected via line 21 into line 13, or it may be added directly into the high shear mixer (not shown), if needed.

In some embodiments, two or more high shear devices like HSD 40, or they may be configured differently, are aligned in series, and are used to further enhance the reaction. Their operation may be in either batch or continuous mode. In some instances in which a single pass or "once through" process is desired, the use of multiple high shear devices in series may also be advantageous. In some embodiments where multiple high shear devices are operated in series, vessel 10 may be omitted. When multiple high shear devices 40 are operated in series, additional reactant(s) may be injected into the inlet feed stream of each device. In some embodiments, multiple high shear devices 40 are operated in parallel, and the outlet emulsions therefrom are introduced into one or more vessel 10.

In embodiments, use of the disclosed system and process comprising reactant mixing via external high shear device 40 allows use of less acid catalyst and/or excess of isoparaffin in high shear system 100 than previously permitted. In embodiments, an external high shear device 40 is incorporated into an established process thereby permitting an increase in production (greater throughput) from a process operated without high shear device 40. In embodiments, much of the reaction occurs within the external high shear device 40. In embodiments, usage of catalyst is reduced when compared to alkylation in the absence of external high shear device 40. In embodiments, the amount of olefin excess is reduced when compared to alkylation in the absence of high shear device 40.

In embodiments, the system and process of the present disclosure provide for a higher alkylate yield from an isoparaffin feedstock than conventional alkylation systems and processes comprising an absence of external high shear mixing. In embodiments, the high shear alkylation system and process of the present disclosure allows the production of an alkylate having a higher octane rating than alkylate obtained from an alkylation reactor in the absence of high shear device 40. In embodiments, the use of the present system and method for the alkylating of isoparaffins makes economically feasible the use of reduced amounts of olefin and/or catalyst by increasing the rate of alkylation, etc.

In some embodiments, the enhanced mixing potentiates an increase in throughput of the process stream. In contrast to some existing methods that attempt to increase the degree of alkylation by increasing reactor pressures, the superior dissolution and/or emulsification provided by external high shear dispersion may allow in many cases a decrease in overall operating pressure while maintaining or even increasing reaction rate. Without wishing to be limited to a particular theory, it is believed that the level or degree of high shear mixing is sufficient to increase rates of mass transfer and may also produce localized non-ideal conditions that permit reactions to occur that might not otherwise be expected to occur based on Gibbs free energy predictions. Localized non ideal conditions are believed to occur within the high shear device resulting in increased temperatures and pressures with the most significant increase believed to be in localized pressures. The increase in pressures and temperatures within the high shear device are instantaneous and localized and quickly revert back to bulk or average system conditions once exiting the high shear device. In some cases, the high shear mixing device induces cavitation of sufficient intensity to dissociate one or more of the reactants into free radicals, which may intensify a chemical reaction or allow a reaction to take place at less stringent conditions than might otherwise be required. Cavitation may also increase rates of transport processes by producing local turbulence and liquid micro-circulation (acoustic streaming). An overview of the application of cavitation phenomenon in chemical/physical processing applications is provided by Gogate et al., "Cavitation: A technology on the horizon," *Current Science* 91 (No. 1): 35-46 (2006). The high shear mixing device of certain embodiments of the present system and methods is operated under what is believed to be cavitation conditions effective to dissociate the reactants into free radicals which then form into alkylate product.

In some embodiments, the system and processes described herein permit design of a smaller and/or less capital intensive process than previously possible without the use of external high shear mixer 40. Potential advantages of certain embodiments of the disclosed processes are reduced operating costs and increased production from an existing process. Certain embodiments of the disclosed processes additionally offer the advantage of reduced capital costs for the design of new processes. Potential benefits of some embodiments of this system and methods for alkylation include, but are not limited to, faster cycle times, increased throughput, higher conversion, reduced operating costs and/or reduced capital expense due to the possibility of designing smaller reactors and/or operating the alkylation process at lower temperature and/or pressure.

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, and so forth). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The disclosures of all patents, patent applications, and publications cited herein are hereby incorporated by reference, to the extent they provide exemplary, procedural or other details supplementary to those set forth herein.

What is claimed is:

1. A method for alkylating a hydrocarbon comprising at least one isoparaffin and at least one olefin, the method comprising:
   introducing a liquid catalyst selected from the group consisting of hydrofluoric acid, $BF_3$, $SbF_5$, and $AlCl_3$, and combinations thereof and the hydrocarbon into a high shear device, wherein the high shear device comprises a rotor and a stator separated by a shear gap;
   processing the liquid catalyst and the hydrocarbon in the high shear device to form an emulsion comprising droplets of hydrocarbon dispersed in the liquid catalyst, wherein the droplets have a mean diameter in the range of about 0.1 µm to about 5 µm;
   introducing the emulsion into a vessel operating under suitable alkylation conditions whereby at least a portion of the isoparaffin is alkylated with the olefin to form alkylate, wherein suitable alkylation conditions comprise a bulk reaction temperature of from about 38° C. to about 90° C. and a bulk reaction pressure in the range of from about 1379 kPa to about 34 MPa; and
   removing a product stream comprising alkylate from the vessel.

2. The method of claim 1, wherein the at least one isoparaffin contains from 4 to 8 carbon atoms.

3. The method of claim 2, wherein the at least one olefin contains from 2 to 12 carbon atoms.

4. The method of claim 3, wherein the at least one isoparaffin is isobutane and the at least one olefin is butene.

5. The method of claim 1, wherein the droplets have a mean diameter of no more than 100 nm.

6. The method of claim 1, wherein forming the emulsion comprises subjecting the hydrocarbon and acid to high shear mixing at a tip speed of at least 22.9 m/s and to a shear rate of greater than about 20,000 $s^{-1}$, and wherein the high shear device produces a local pressure of at least about 1034 MPa at the tip.

7. The method of claim 1, wherein the shear gap has a width in the range of from about 0.02 mm to about 5 mm, and wherein the rotor and the stator each comprise at least one toothed surface.

8. A method for alkylating a hydrocarbon comprising at least one isoparaffin and at least one olefin, the method comprising:
   introducing a liquid catalyst selected from the group consisting of hydrofluoric acid, $BF_3$, $SbF_5$, $AlCl_3$, and combinations thereof, and the hydrocarbon into a high shear device comprising at least one rotor and at least one stator separated by a shear gap width;
   processing the liquid catalyst and the hydrocarbon in the high shear device to form an emulsion comprising droplets having a mean diameter less than about 5 µm; and transferring the emulsion from the high shear device into a vessel operating under suitable alkylation conditions whereby at least a portion of the isoparaffin is alkylated with the olefin to form alkylate.

9. The method of claim 8, wherein the at least one isoparaffin contains from 4 to 8 carbon atoms.

10. The method of claim 9, wherein the at least one olefin contains from 2 to 12 carbon atoms.

11. The method of claim 10, the method further comprising removing a product stream comprising alkylate from the vessel, wherein the droplets have a mean diameter of no more than 100 nm.

12. The method of claim 10, wherein the shear gap is in the range of from about 0.02 mm to about 5 mm, and wherein the rotor and the stator each comprise at least one toothed surface.

13. The method of claim 10, wherein the emulsion comprises hydrocarbon droplets dispersed in the liquid catalyst, and wherein the mean diameter is less than 1 micron.

14. The method 10, wherein the emulsion comprises catalyst droplets dispersed in the hydrocarbon, and wherein the mean diameter is less than 1 micron.

15. The method of claim 10, wherein the mean diameter is also greater than about 0.1 µm.

16. A method for alkylating a hydrocarbon comprising at least one isoparaffin and at least one olefin, the method comprising:
   introducing a liquid catalyst and the hydrocarbon into a high shear device comprising at least one rotor and at least one stator separated by a shear gap width, wherein the liquid catalyst comprises an acid selected from the group consisting of hydrofluoric acid, $BF_3$, $SbF_5$, $AlCl_3$, and combinations thereof;
   forming an emulsion comprising hydrocarbon droplets dispersed in the liquid catalyst, wherein the droplets have a mean diameter of less than about 5 µm; and
   introducing the emulsion into a vessel operating under suitable alkylation conditions whereby at least a portion of the isoparaffin is alkylated with the olefin to form alkylate, wherein suitable alkylation conditions comprise a bulk reaction temperature of from about 38° C. to about 90° C. and a bulk reaction pressure in the range of from about 1379 kPa to about 34 MPa.

17. The method of claim 16, wherein the mean diameter is also greater than about 0.1 µm.

* * * * *